Figure 1:
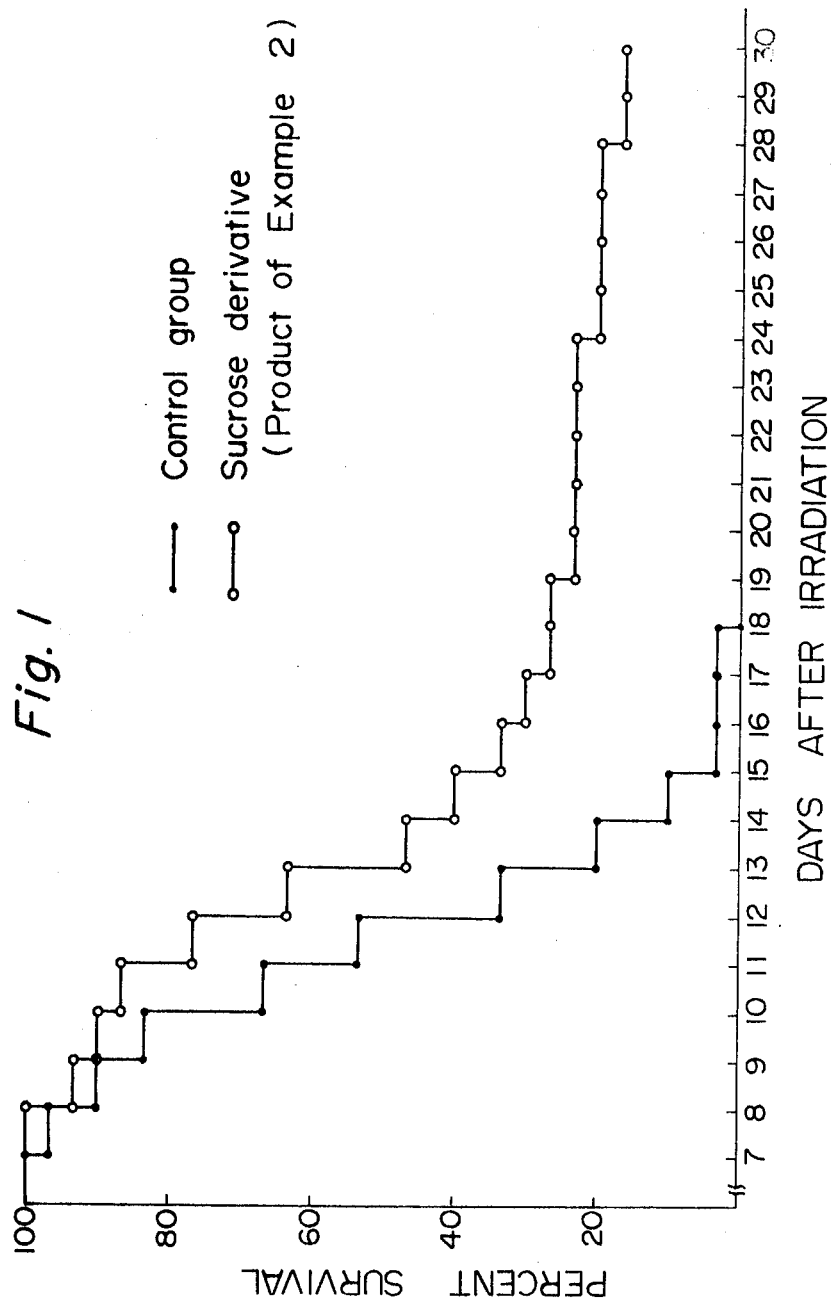
Figure 2:
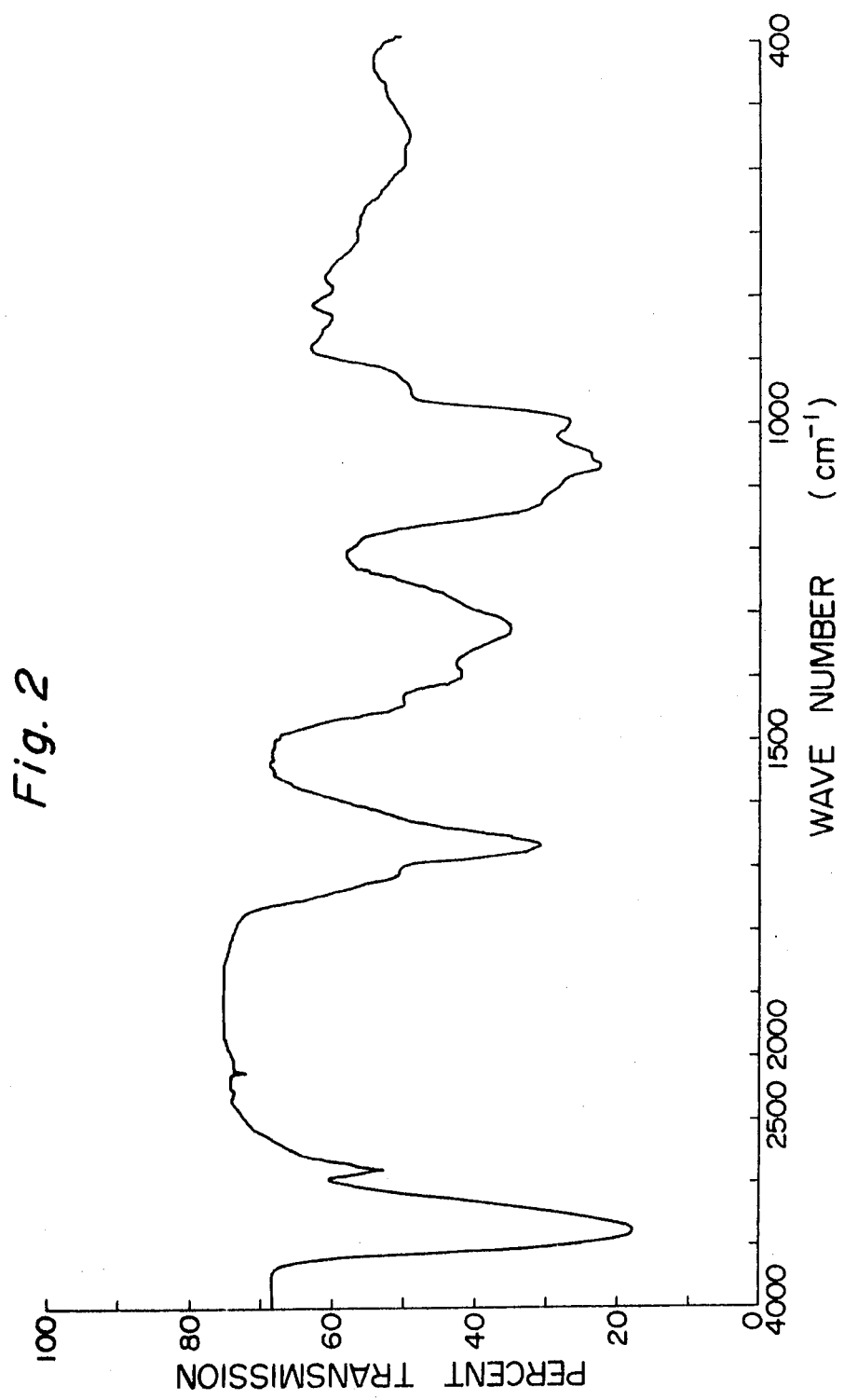
Figure 3:
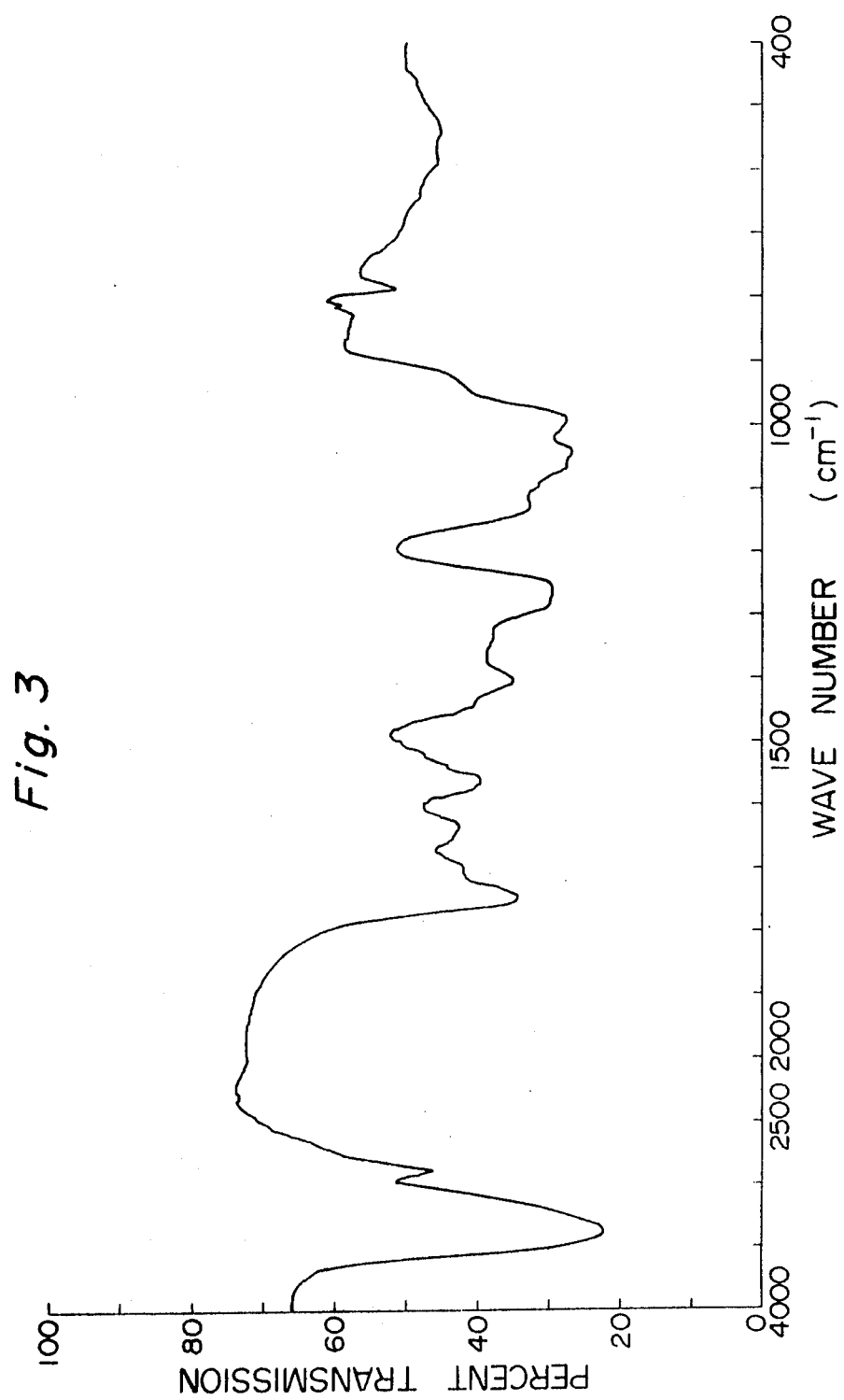
Figure 4:
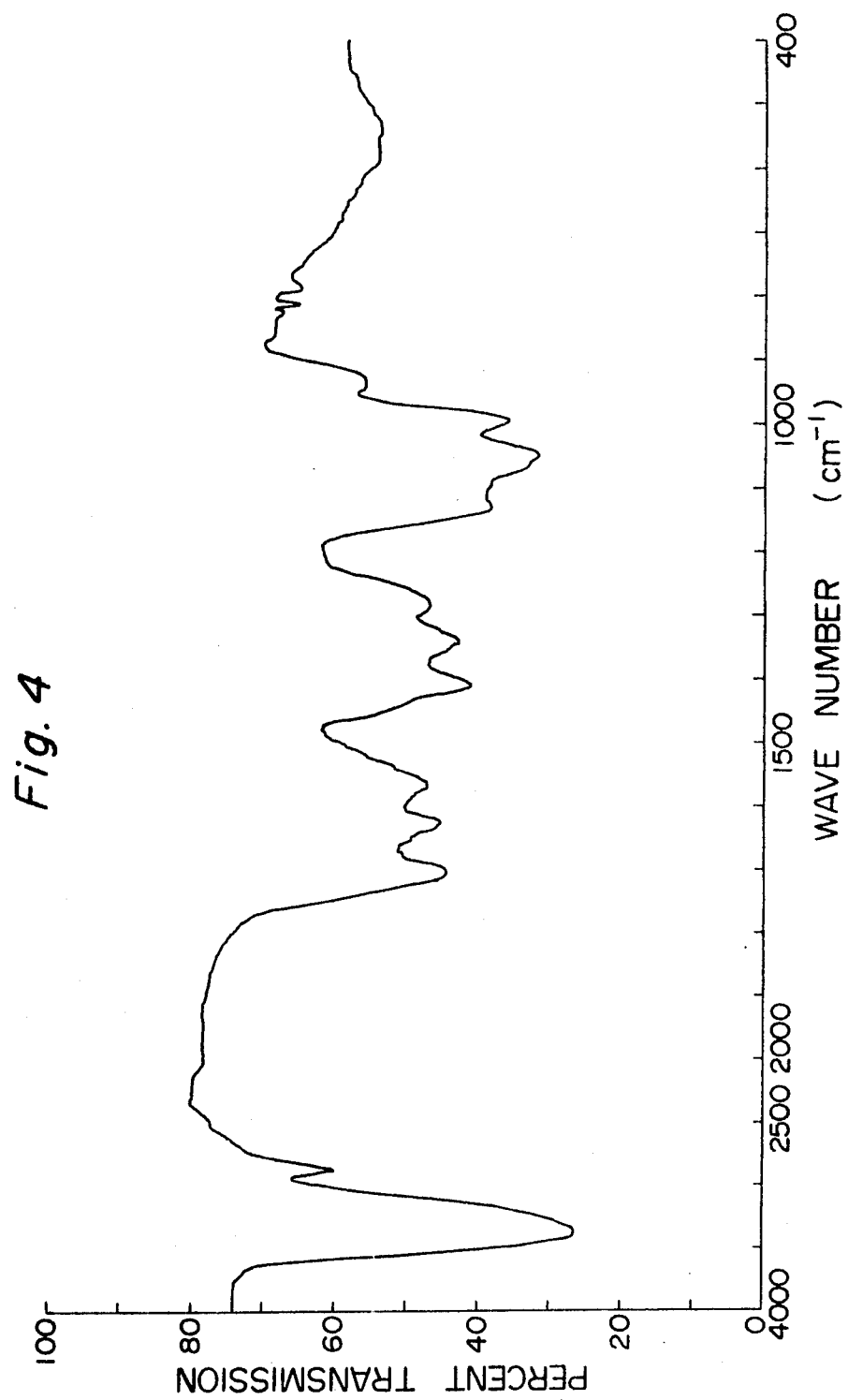
Figure 5:
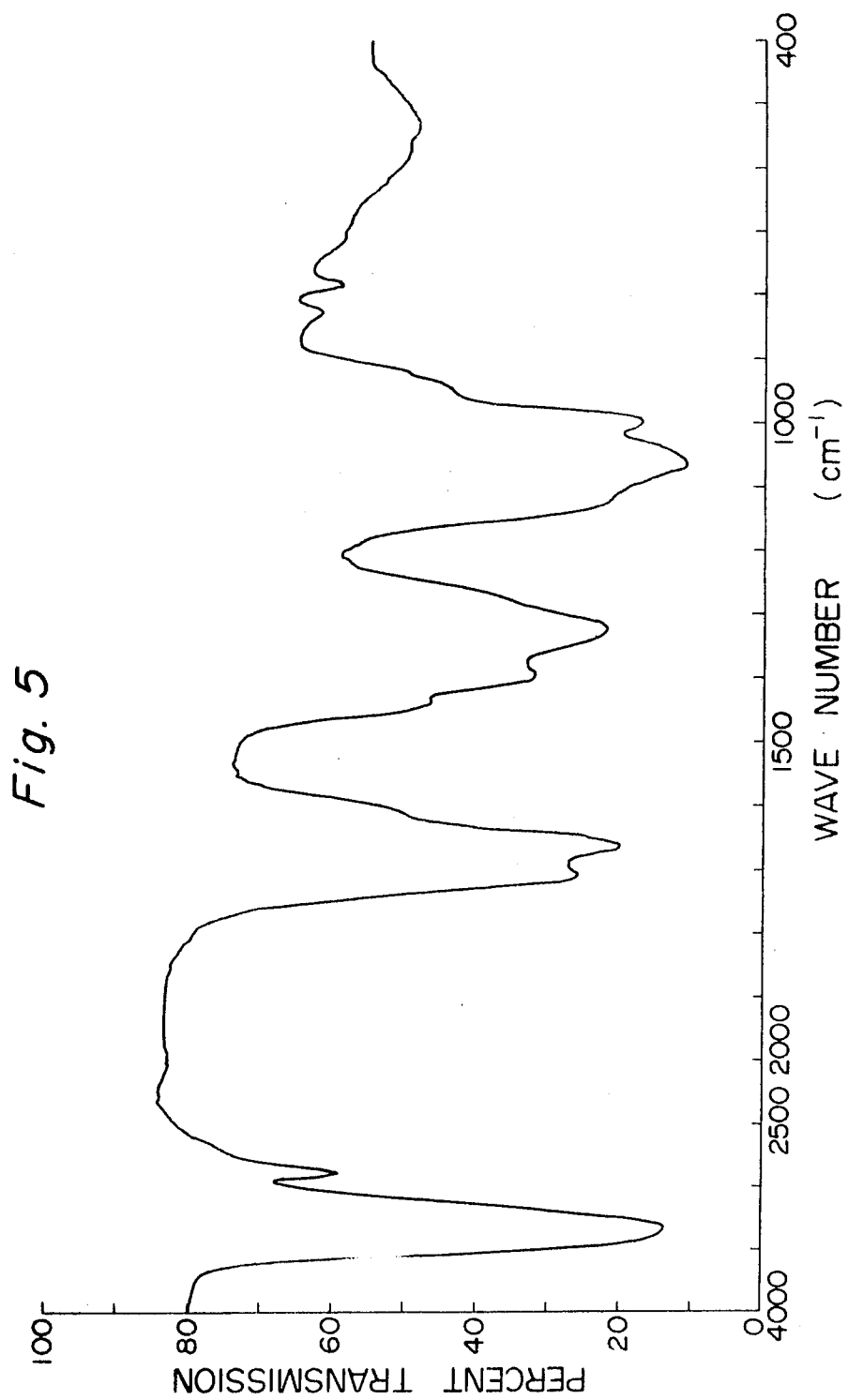
Figure 6:
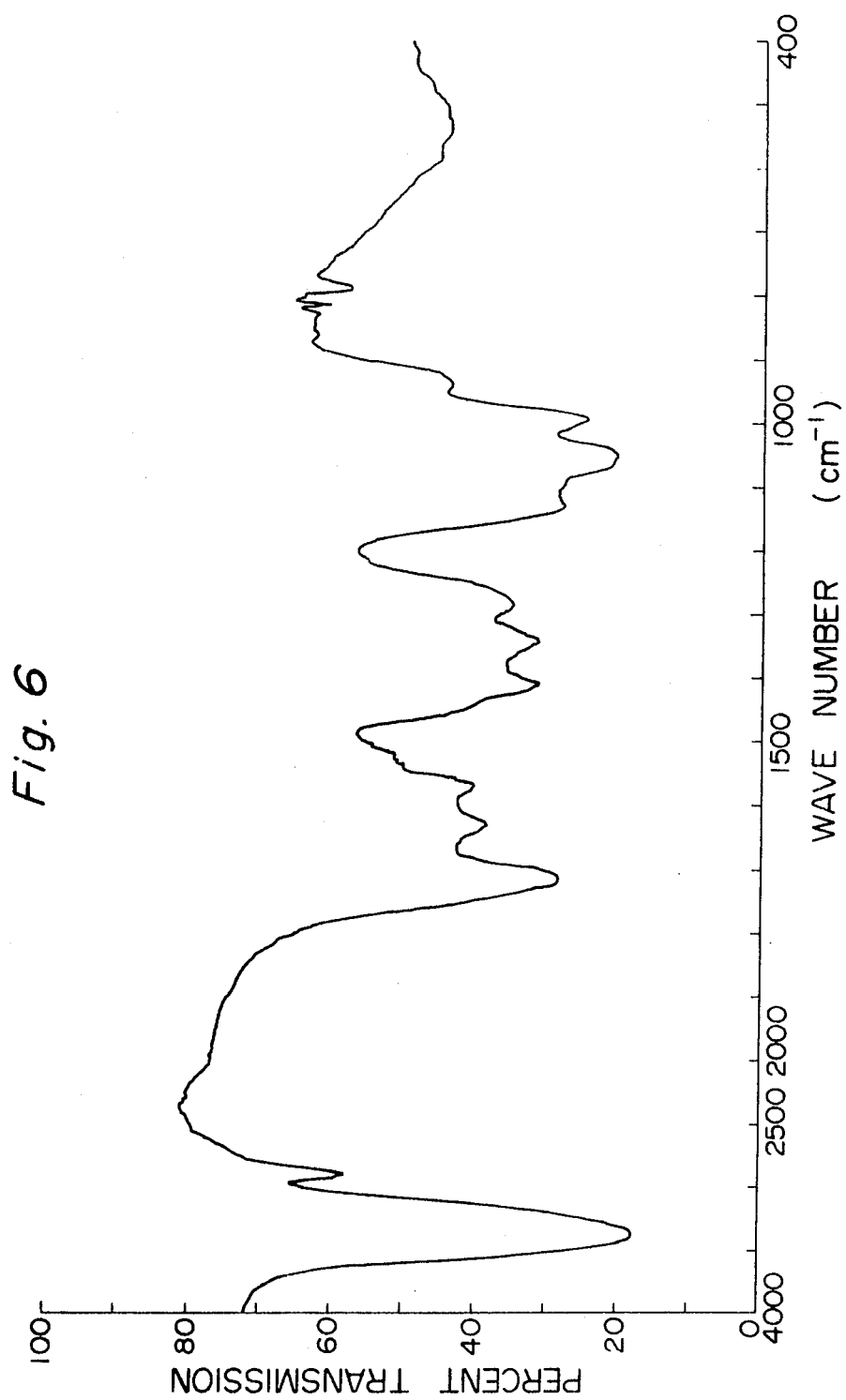
Figure 7:
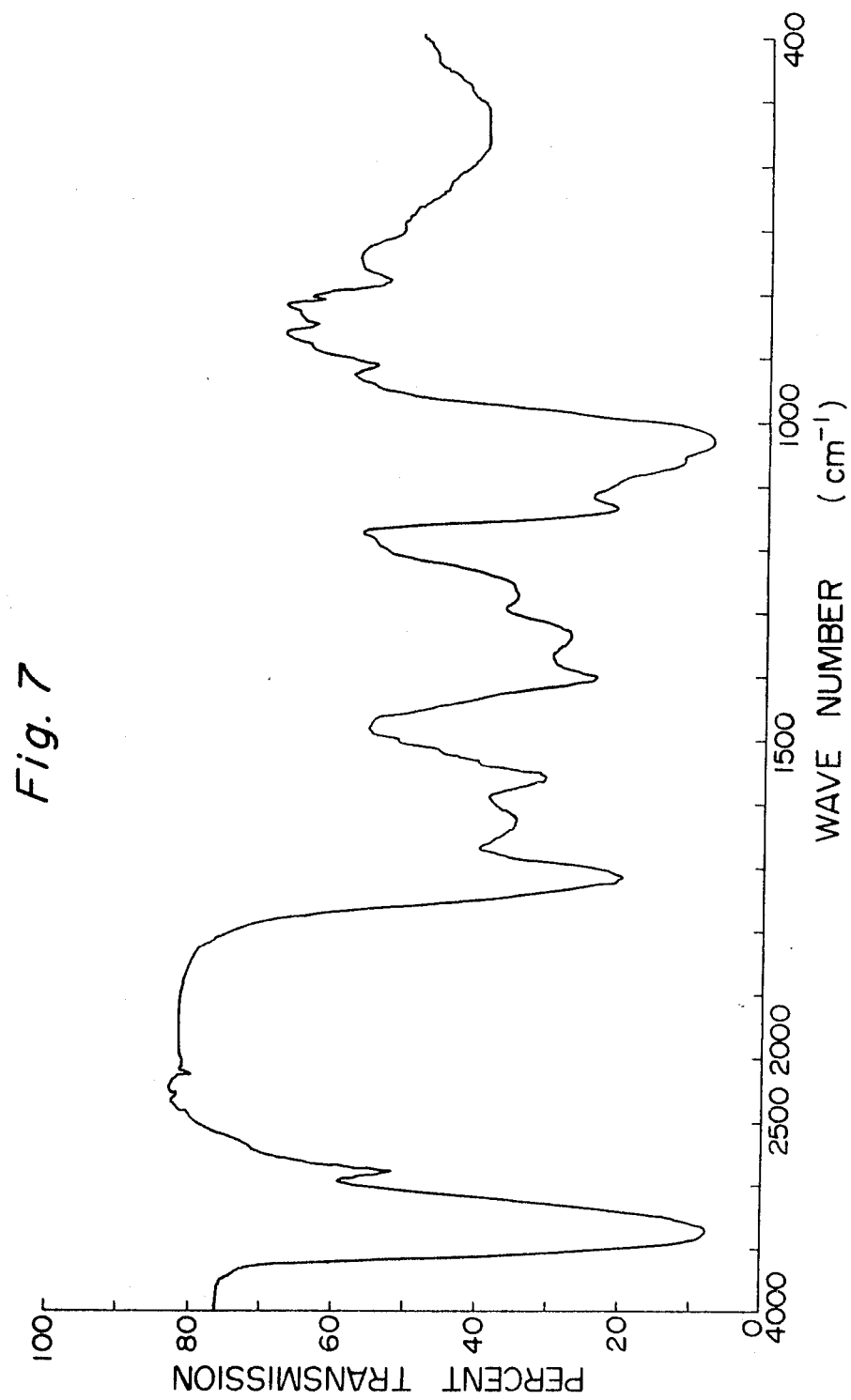
Figure 8:
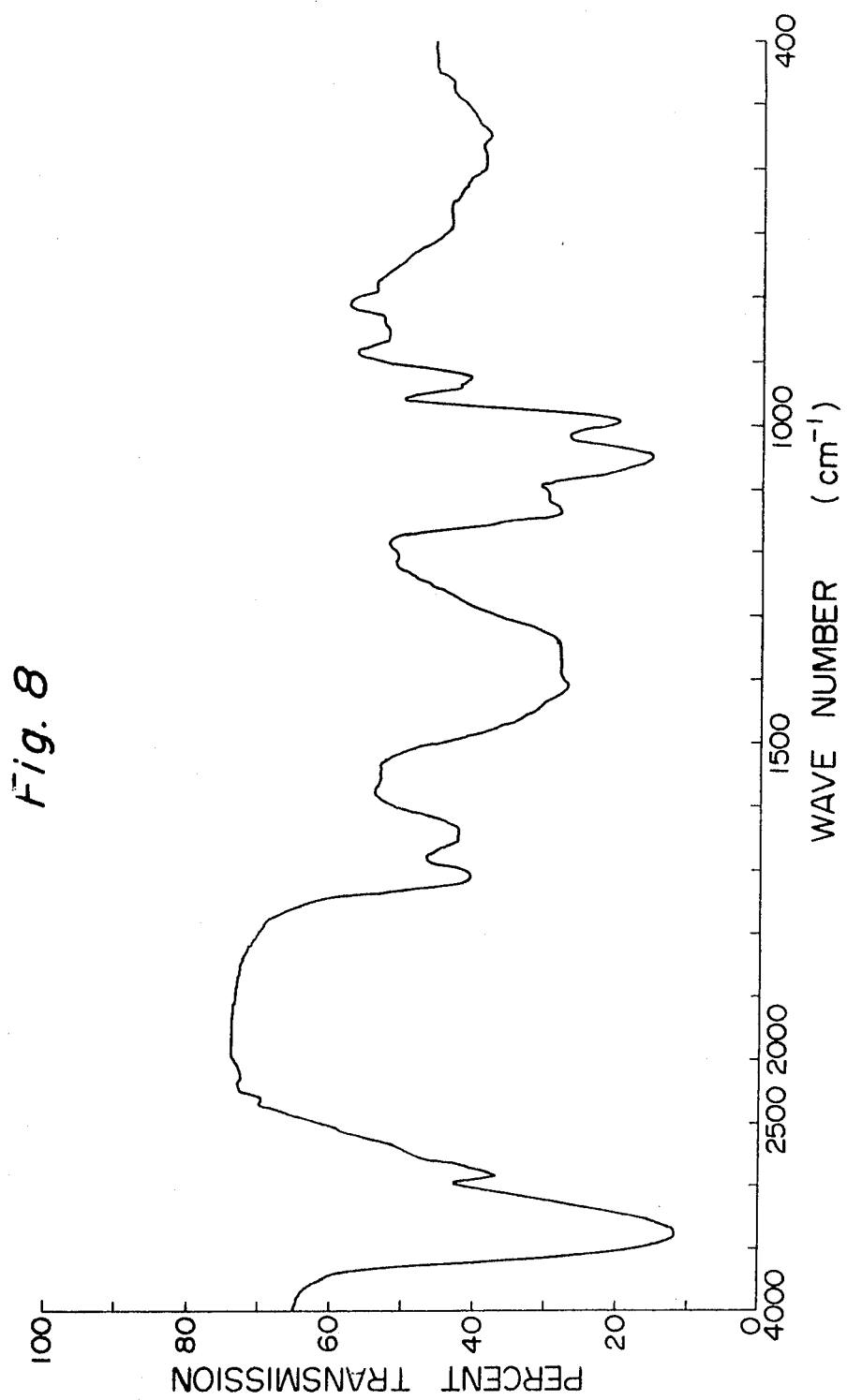
Figure 9:
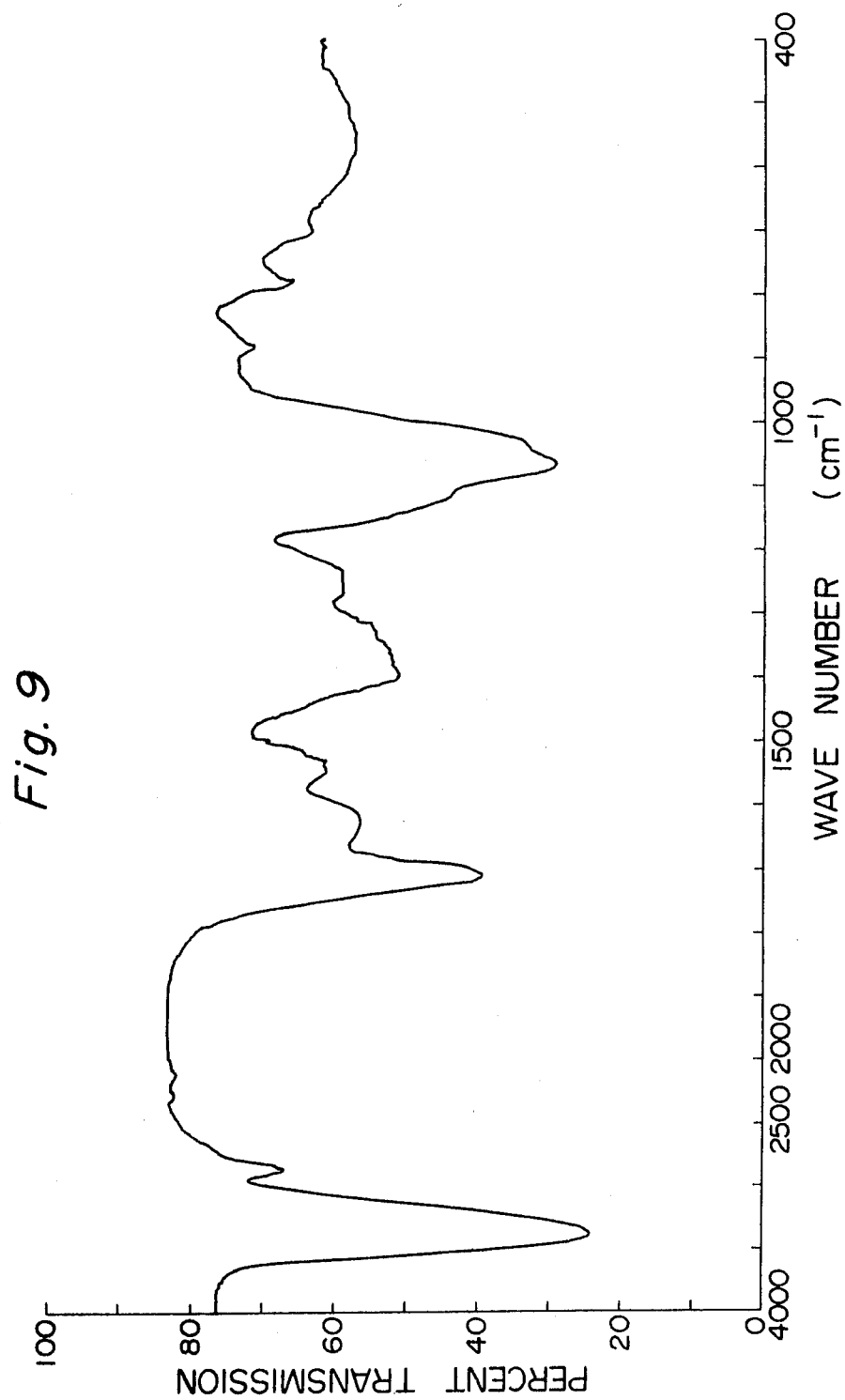
Figure 10:
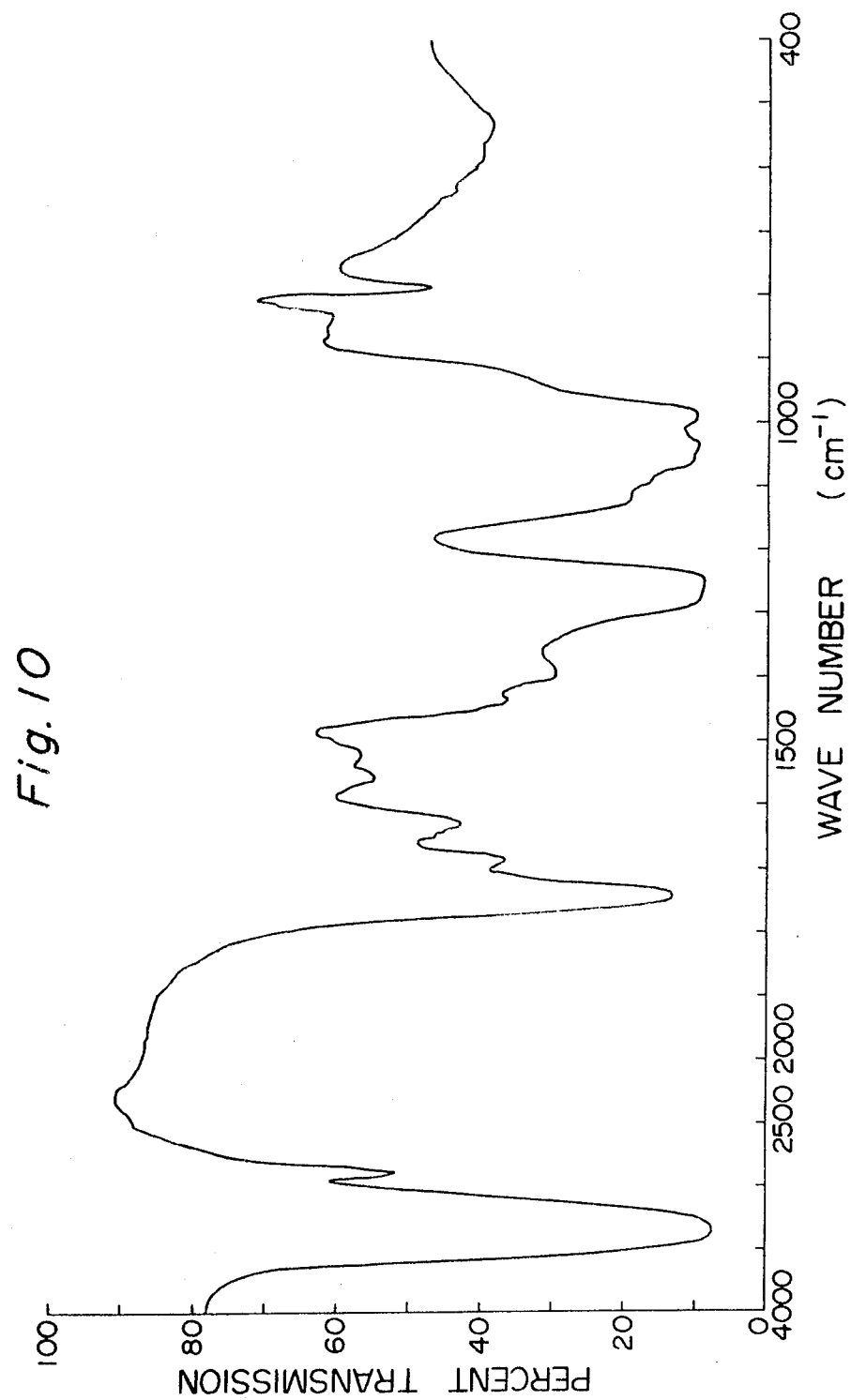
Figure 11:
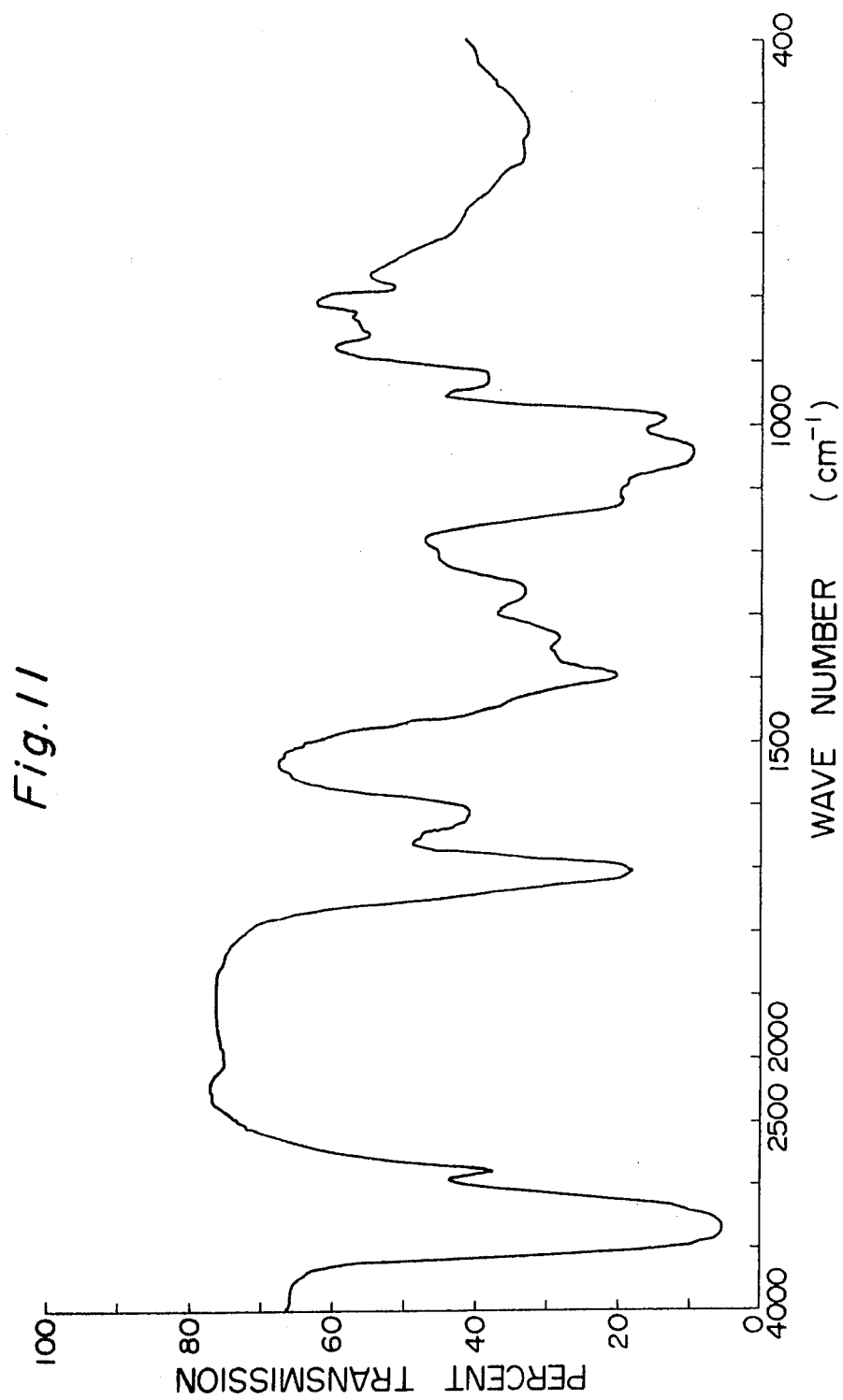

United States Patent [19]

Mizutani et al.

[11] 4,080,442

[45] Mar. 21, 1978

[54] DISACCHARIDE DERIVATIVES USED IN THE TREATMENT OF HEPATIC DISEASES

[75] Inventors: Akihiro Mizutani, Nagoya; Kyoji Kito, Seto; Hideki Miyaji, Nagoya; Taketoshi Komori, Gifu; Takao Ogawa, Nagoya; Hideo Nagae, Kasugai; Hiromi Hanai, Nagoya, all of Japan

[73] Assignee: Meito Sangyo Kabushiki Kaisha, Nagoya, Japan

[21] Appl. No.: 623,049

[22] Filed: Oct. 16, 1975

[51] Int. Cl.² .................... A61K 31/70; C07G 3/00
[52] U.S. Cl. .................................. 424/180; 536/1; 536/115
[58] Field of Search ................. 424/180; 536/1, 115

[56] References Cited

PUBLICATIONS

Merck Manual (1972), pp. 770–783.
Dressler, Chemical Abstracts 72:77184g, (1970).

*Primary Examiner*—Leonard Schenkman
*Attorney, Agent, or Firm*—Sherman and Shalloway

[57] ABSTRACT

A pharmaceutical composition containing as its active ingredient a disaccharide derivative having a derivative group of the following formula (1) bonded to a carbon atom of a disaccharide:

$$(-O-\overset{Y}{\underset{\parallel}{C}}-Z) \qquad (1)$$

wherein Y is a member of the group consisting of NH and O; and when Y is NH, Z is a member of the class consisting of —O—(disaccharide residue) and —O—, with the proviso that one of the two bonds is attached to the other carbon atom of the same disaccharide to which the formula (1) group is bonded, and when Y is O, Z is a member of the class consisting of —NH$_2$ and —O—, with the proviso that one of the two bonds is attached to a carbon atom of a disaccharide different from that to which the formula (1) group is bonded. The disaccharide derivative can be prepared by reacting a disaccharide with an activating agent selected from the group consisting of the cyanogen halides, organic cyanic acid esters and halogenocarbonic acid alkyl esters. Said pharmaceutical composition is useful for treating hepatic diseases.

21 Claims, 14 Drawing Figures

DISACCHARIDE DERIVATIVES USED IN THE TREATMENT OF HEPATIC DISEASES

This invention relates to disaccharide derivatives which as a treating agent of, for example, hepatic diseases and radiation damage of animals (a generic term which includes domestic fowls and animals in addition to man in this invention) are useful for the treatment of such diseases; as well as a process for the preparation of such disaccharide derivatives and pharmaceutical compositions containing said derivatives as an active ingredient.

More specifically, the invention relates to disaccharide derivatives having a derivative group of the following formula (1) bonded to a carbon atom of a disaccharide:

(1)

wherein Y is either NH or O; and when Y is NH, Z is either —O— (disaccharide residue) or —O—, with the proviso that one of the two bonds is attached to the other carbon atom of the same disaccharide to which the formula (1) group is bonded, and when Y is O, Z is either —NH$_2$ or —O—, with the proviso that one of the two bonds is attached to a carbon atom of a disaccharide differing from that to which the formula (1) group is bonded; as well as a process for preparing such disaccharide derivatives and pharmaceutical compositions containing said derivatives as an active ingredient.

It is known to prepare complexes by reacting the various biopolymers such as chymotrypsin, insulin, gamma-globulin, oxytocin and glucose oxidase with the activated polysaccharides they have been obtained by reacting a polysaccharide or derivative thereof such as dextran, cellulose, starch, dextrin, hydroxyethyl cellulose, p-amino phenoxy hydroxy propyl dextran and agarose with a cyanogen halogenide (British Pat. No. 1,223,281) or an organic cyanic acid ester (Japanese Pat. Publication No. 28031/74).

According to this conventional proposal, it is disclosed that it is possible to chemically bound said biopolymers with the polysaccharides or derivatives thereof with no substantial loss of the activities or abilities that are possessed by the biopolymers.

Further, in another similar suggestion (West German Laid-Open Pat. No. 2,413,512) there is disclosed the preparation of complexes by reacting the polysaccharides such as hereinbefore indicated with the amino or amido group-containing pharmacologically or therapeutically active compounds such as dimethofrine and insulin.

In this prior art proposal there is a disclosure to the effect that the resulting complex not only does not lose its pharmacological activity but also possesses it lastingly.

A common feature of these conventional proposals is that they teach the preparation of complexes by reacting medicinal compounds as well as biopolymers with the activated polysaccharides and that the so obtained complexes are useful. However, there is no disclosure at all concerning the usefulness of the activated polysaccharides themselves. Further, while these conventional proposals disclose in common concerning the reaction between the polysaccharides or derivatives thereof and the medicinal compounds as well as biopolymers, they completely lack an awareness of the active compounds of the oligosaccharides.

We furthered our research into the oligosaccharides, and especially the disaccharides, and, as a consequence, discovered to our surprise that the disaccharide derivatives having the foregoing derivative group of formula (1) bonded to a carbon atom of the disaccharide (hereinafter to be referred to as activated disaccharides in this invention) demonstrated in themselves excellent utility as a treating agent for a wide range of hepatic and allergic diseases and radiation damage of animals when used in the treatment of these diseases.

The aforementioned disaccharide derivatives are compounds that have not been disclosed in publications published prior to the filing date of the instant application for letters patent. Furthermore, they are compounds whose utility for medical purposes ws entirely unexpected. In this sense, the present invention is a pioneer invention in the field of disaccharide derivatives.

It is therefore an object of this invention to provide the foregoing disaccharide derivatives, a process for their preparation, and pharmaceutical compositions containing said derivatives as an active ingredient.

Another object of the invention is to provide a method of treating hepatic and allergic diseases and radiation damage of animals suffering from these disorders by administering the foregoing disaccharide derivatives.

Other objects and advantages of the present invention will become apparent from the following description.

The compounds of the present invention are disaccharide derivatives having the foregoing formula (1) derivative group bonded to a carbon atom of a disaccharide.

The foregoing disaccharide derivatives having a derivative group, if shown archetypically, can be shown by the following four types of model forms.

When Y is NH:

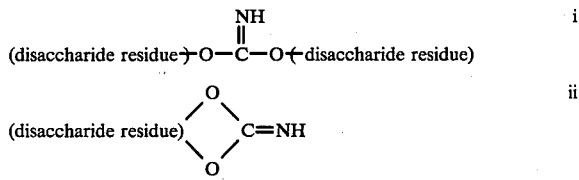

When Y is O:

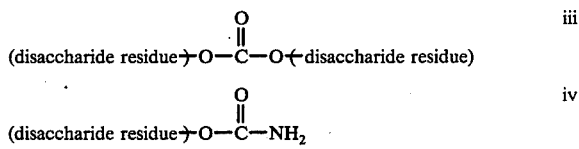

The above examples are model forms, and in the case of the derivative groups of i, iii and iv, above, one disaccharide residue can have a maximum of eight of the derivative groups of the foregoing formula (1), while in the case of the derivative group of ii, above, one disaccharide can have a maximum of four of the derivative groups of formula (1). Further, there can be introduced to one disaccharide residue an optional combination of derivative groups of the foregoing four types up to the maximum indicated above. Hence, it is possible to connect a plurality of different types of the foregoing model forms, or it is possible to connect a plurality of the same types in the case of the i and iii types. The inherent viscosity of the disaccharide derivatives of the present invention is usually above about 0.018 dl/g, and most usually about 0.018 to about 0.080 dl/g. Again, the disaccharide derivatives of the invention are usually a white to light yellowish powder and usually has an infrared spectrum which exhibits characteristic absorption bands at at least one of the neighborhoods of 1680 cm$^{-1}$, 1715 cm$^{-1}$ and 1750 cm$^{-1}$.

The "inherent viscosity", as used herein, is indicated by $[\eta]$, which is defined as follows:

$$[\eta] = \lim_{c \to 0} \eta_{sp/c}$$

wherein
$\eta_{sp} = (\eta - \eta_o)/\eta_o = \eta/\eta_o - 1$
$\eta$ is the viscosity of the sample solution (1.0 M in an isotonic salt solution at 25° C.)
$\eta_o$ is the viscosity of the solvent
c is the concentration in g/100 ml In the case of water-insoluble disaccharide derivative the sample solution is prepared in the following manner. 1.2 Grams of the sample is added to 50 milliliters of 2N-NaOH aqueous solution and dissolved therein by heating for one hour at 70° C. After the solution cools, it is neutralized with an aqueous HCl solution to pH 7, after which water is added to bring the total volume to 100 millimeters.

The disaccharide derivatives of this invention can be prepared by reacting a disaccharide with an activating agent selected from the group consisting of the cyanogen halides, organic cyanic acid esters and halogenocarbonic acid alkyl esters. As the foregoing disaccharides, there can be mentioned such disaccharides as, for example, sucrose, lactose, maltose and isomaltose. In the case where a cyanogen halide and/or an organic cyanic acid ester is used as the activating agent, the reaction can be carried out in an aqueous medium or a lower alcohol medium such as methanol or ethanol or a mixed medium thereof. However, water is preferred. The reaction can be carried out after adding to the medium a buffer such as the carbonates or bicarbonates of an alkali metal such as lithium, sodium and potassium. Good results are had by such an addition. The reaction is preferably carried out under alkaline conditions, preferred being a pH of about 9 to about 12, and more preferably about 9.5 to about 11.5. The reaction proceeds even at a temperature of below 0° C. Thus, the employment of a temperature in a range from the temperature at which the reaction system does not freeze to about 40° C. will do, preferred being a temperature ranging between about 0° C. and about 350° C. The reaction can be carried out for a period of usually about 5 minutes to about 24 hours preferably with stirring. The reaction may be carried out until at least partial hydrolysis of the resulting disaccharide derivative takes place, or the hydrolysis can be carried out after the disaccharide derivative has been separated.

Specific examples of the aforementioned cyanogen halides and organic cyanic acid esters, the activating agents, include such compounds as cyanogen bromide, cyanogen iodide, cyanogen chloride, phenyl cyanate and 2,2,2-trichloroethyl cyanate.

On the other hand, when the reaction is to be carried out using a halogenocarbonic acid alkyl ester as the activating agent, the disaccharide is reacted with a halogenocarbonic acid ester, preferably a chloro- or bromocarbonic acid lower alkyl ester such, for example, as methyl chlorocarbonate and ethyl bromocarbonate, in an organic solvent such, for example, as dimethyl sulfoxide, tetrahydrofuran, dioxane, toluene, chloroform, ethyl acetate and mixtures of these solvents at preferably a temperature of about $-15°$ C. to about $+30°$ C. in the presence of a $C_1$-$C_4$ trialkylamine, preferably a tertiary amine, such, for example, as triethylamine and tributylamine. It is preferred that the reaction product be at least partially hydrolyzed.

While there is imposed no particular restriction as to the ratio in which the aforementioned disaccharide and the activating agent selected from the group consisting of the cyanogen halides, organic cyanic acid esters and halogenocarbonic acid esters are reacted, a weight ratio of the disaccharide to activating agent of 1: about 0.1 – about 3.5 is preferred. The concentration of the disaccharide is preferably about 10% to about 20% (weight/solvent volume), while the concentration of the activating agent is preferably about 5% to about 15% (weight/solvent volume).

After completion of the reaction, the reaction solution is mixed with about 1 – 20-fold amount (volume) of an organic solvent, e.g., methanol, ethanol, acetone, methyl ethyl ketone and ethyl ether at low temperature conditions of, say, $-10°$ C. to $+10°$ C., to form an activated disaccharide precipitate, which can then be collected. If desired, the precipitate is then washed thoroughly with cold acetone or ethyl ether. Further, the so obtained activated disaccharide can be purified by the following procedure. The activated disaccharide is dissolved in an aqueous medium of pH 2 – 11, preferably 5 – 9, using, if necessary, an acid or an alkali. The resulting solution is then stirred for 5 minutes to 48 hours at 0° – 50° C., and preferably below 30° C., after which an organic solvent identical to that indicated hereinabove is added to cause the activated disaccharide to be precipitated in an at least partially hydrolyzed form. As the acids or alkalis to be used in a hydrolysis such as described, there can be mentioned such, for example, as the alkaline substances as the hydroxides of the alkali metals such as lithium, sodium and potassium, the carbonates of these metals, the bicarbonates of these metals, and ammonia; the mineral acids such as hydrochloric acid and sulfuric acid; the organic acids such as acetic acid and tartaric acid; and the buffer solutions such as the buffer solution consisting of ammonia and ammonium chloride, the buffer solution consisting of sodium carbonate and sodium bicarbonate, the buffer solution consisting of acetic acid and sodium acetate and the buffer solution consisting of borax and hydrochloric acid.

On the other hand, when the reaction product is water-insoluble, it can be purified, say, by a procedure consisting of filtering or centrifuging the reaction product and thereafter washing it in, for example, cold acetone, cold methanol or cold water.

The invention disaccharide derivative obtained in this manner can then be dried by any of such drying methods as vacuum drying, spray drying or freeze drying. The drying is preferably carried out at the lowest possible temperature. For example, preferred is a temperature of below about 60° C., but in the case of spray drying a higher temperature can be used. It is possible to obtain according to this invention disaccharide derivatives ranging from those which are water-soluble to those which are water-insoluble by a suitable choice of the reaction conditions.

It is possible in accordance with this invention to provide a pharmaceutical composition consisting of a pharmaceutically effective amount of the above-described disaccharide derivative and a pharmaceutically acceptable diluent, as well as a method of treating the hepatic or allergic diseases or radiation damage of animals by administering the foregoing disaccharide derivative.

The disaccharide derivatives of this invention demonstrate superior effects in the treatment of the hepatic diseases e.g., acute hepatitis, cholangiolitic hepatitis, fatty liver, drug-induced hepatic injury, hepato-cirrhosis, intoxication, or the allergic diseases, e.g., allergic coryza, hives, drug eruptions, eczema, or the radiation damage e.g., leukopenia due to radiogenic disorders and radiation hangover. In addition, the invention disaccharide derivatives have an exceedingly low toxicity. In general, the disaccharide derivatives of this invention have an acute toxicity $LD_{50}$ value demonstrating an extremely low toxicity, of usually at least 20 g/kg when intravenously injected into mice.

The pharmaceutical composition of this invention should usually contain, based on the weight of the composition, 1 – 90% by weight of the foregoing disaccharide derivative. The foregoing content can be suitably varied in accordance with the form of the preparation.

The disaccharide derivatives of this invention can be blended with a pharmaceutically acceptable diluent and can be used in the form of such orally administered preparations as, for example, a powder, granules, capsules, tablets, coated tablets, a syrupy preparation, aqueous solutions, etc., as well as non-orally administered preparations such as injection preparations.

As the foregoing diluents, there can be mentioned the various liquid or solid diluents. Examples of the pharmaceutically acceptable solid diluents include calcium phosphate, calcium carbonate, dextrose, sucrose, dextrin, sucrose ester, starch, sorbitol, mannitol, crystalline cellulose, talc, kaolin, synthetic aluminum silicate, carboxy methyl cellulose, methyl cellulose, cellulose acetate phthalate, sodium alginate, polyvinyl pyrrolidone, polyvinyl alcohol. gum arabic, tragacanth gum, gelatin, agar powder and shellac. On the other hand, the pharmaceutically acceptable liquids include such, for example, as water, isotonic salt solution, ethanol, propylene glycol, polyethylene glycol, glycerol, Hartman's solution and Ringer's solution.

The disaccharide derivatives of this invention can be used in a dosage of usually about 5 milligrams to 250 milligrams per kilogram body weight per day.

Further, the pharmaceutical composition of this invention can be used as a physical mixture with other medicines. Again, the invention composition can be used in conjunction with other medicines in the treatment method of this invention. As such substances to be used as a mixture or in conjunction with the invention composition, included are such, for example, as glutathione, cysteine, methionine and N-(2-mercaptopropionyl)-glycine. Especially preferred is a physical mixture of the invention composition with glutathione or the case where the latter is administered conjointly with the invention composition. For this purpose, either the oxidized or reduced type of glutathione can be used. As compared with the case where the invention disaccharide derivatives and these other substances are used independently of each other, synergistic effects are demonstrated when these physical mixtures are used or when the invention disaccharide derivatives and these other substances are conjointly administered, the synergistic effects being especially marked when the invention disaccharide derivatives and glutathione are used as a physical mixture or are conjointly administered. It was truly surprising that the oxidized type glutathione which hitherto had been considered as being ineffective for the treatment of the hepatic diseases, could be used for achieving the aforementioned improvement. Hence, there is provided in accordance with this invention a pharmaceutical composition which consists of pharmaceutically effective amounts of a disaccharide derivative of this invention and a glutathione selected from the group consisting of the oxidized type glutathione and the reduced type glutathione, and a pharmaceutically acceptable diluent. Again, there is provided a method of treating the hepatic or allergic diseases and radiation damage of animals by the conjoint administration in pharmaceutically effective amounts of a disaccharide derivative of this invention and one of the aforesaid glutathiones. The effective amounts or dosages to be used in these modes, the class of diluents and the forms of the preparations are as hereinbefore described.

In the above modes of the present invention the proportion in which the foregoing glutathiones can be used relative to the disaccharide derivative can be varied over a broad range. For example, the glutathiones can be used preferably in an amount of from about 2 to about 50% by weight, and more preferably 5 – 20% by weight based on the disaccharide derivative.

Experiments which were conducted for determining the pharmaceutical effects of the disaccharide derivatives of this invention when used for the treatment of the hepatic or allergic diseases and radiation damage are described hereinafter.

I. Experimental hepatitis induced by D-galactosamin.

Groups each of 10 female Wistar rats of 100 – 120 gram body weight put on a fast of 2 hours prior to the experiment were used. Solutions of 150 milligrams of the sucrose derivatives obtained in the hereinafter-given Examples 1 - 3 in 1.0 milliliter of isotonic salt solutions were intravenously administered severally to three groups of rats (AS administered groups), while the control group of rats was administered only 1.0 milliliter of the isotonic salt solution. One hour after these administrations, all of the groups were administered with D-galactosamin. The administration of the D-galactosamin was performed in the following manner. A solution of 45 milligrams of D-galactosamin hydrochloride in 1.0 milliliter of an isotonic salt solution was adjusted to a pH of 7.0 with 0.1 N sodium hydroxide, and the so prepared solution was administered abdominally. After completion of this administration, the fasted state was continued. Twenty-two hours after the administration of the D-galactosamin hydrochloride, blood was taken from the abdominal aorta and measured for the GOT, GPT, bilirubin and blood glucose contained in the blood plasma. The GOT and GPT were measured by the Reitman-Frankel Method, the bilirubin by the Evelyn-Malloy Method and the blood glucose by the o-aminobiphenyl method. The results obtained are shown in the following Table 1.

Table 1

| | Control Group | AS Administered Groups | | |
|---|---|---|---|---|
| | | Example 1 | Example 2 | Example 3 |
| GOT (Karmen U.) | 2748±490 | 1120±211** | 1058±229** | 1010±235** |

Table 1-continued

|  | Control Group | AS Administered Groups | | |
| --- | --- | --- | --- | --- |
|  |  | Example 1 | Example 2 | Example 3 |
| GPT (Karmen U.) | 1830±432 | 405±183** | 428±176** | 430±160** |
| Bilirubin (mg/dl) | 0.32±0.04 | 0.21±0.02* | 0.20±0.02* | 0.21±0.03* |
| Blood glucose (mg/dl) | 63±2.3 | 95±7.5** | 98±7.1** | 103±7.3** |

Average value ± S.E.
*P < 0.05
**P < 0.01
AS administered groups: Sucrose derivatives As is apparent from the results given in Table 1, above, in the case of the control group, marked increases in the GOT, GPT and bilirubin in the blood plasma and a decrease in the blood glucose as a results of the development of liver disorders are noted. On the other hand, it can be appreciated that in the case of the groups administered in advance with the sucrose derivatives of this invention these tendencies to increases and decrease in these substances have been checked to a marked degree.

II. Carbon tetrachloride-induced hepatic injury.

(1) Groups each of 10 male Wistar rats of 150 - 200 gram body weight put on a fast of 18 hours prior to the experiment were used. A 1:4 (volume ratio) liquid mixture of carbon tetrachloride and olive oil was injected subcutaneously to the backs of the rats in a dosage of 0.5 milliliter per kilogram, calculated as carbon tetrachloride, following which the fast was continued for 24 hours. Solutions of 300 milligrams of the sucrose derivatives obtained in the hereinafter-given Examples 1 - 3 in 2 milliliters of isotonic salt solutions were administered intravenously to the rats three times (24, 12 and 1 hour before administering the carbon tetrachloride) (AS administered groups). On the other hand, the control group was administered in like manner but with 2 milliliters of only an isotonic salt solution. Blood was then taken in each case from the abdominal aorta 48 hours after the administration of the carbon tetrachloride and the GOT and GPT in the blood plasma were measured by the aforementioned methods. The results obtained are shown in Table 2, below.

Table 2

|  | Control Group | As Administered Groups | | |
| --- | --- | --- | --- | --- |
|  |  | Example 1 | Example 2 | Example 3 |
| GOT (Karmen U.) | 3118±520 | 1662±327* | 1372±262** | 1862±289* |
| GPT (Karmen U.) | 1159±133 | 569±47** | 369±67** | 770±115* |

Average value ± S.E.
*P < 0.05
**P < 0.01
AS administered groups: Sucrose derivatives As is apparent from the results given in Table 2, above, in the case of the control group, marked increases in the GOT and GPT in the blood plasma due to the development of liver damage were noted. In contrast, in the case of groups administered with the sucrose derivatives, it can be seen that the tendency to increases in these substances was checked to a marked degree.

(2) Next, an experiment that was conducted for judging the effects of the invention disaccharide derivatives in curing hepatic injury will be described.

Groups each of 10 male Wistar rats of 150 - 200 gram body weight put on a fast of 18 hours prior to the experiment were used. Rats suffering from hepatitis were prepared by injecting subcutaneously to their backs a 1:4 (volume ratio) liquid mixture of carbon tetrachloride and olive oil in a dosage of 0.5 milliliters per kilogram, calculated as carbon tetrachloride, followed by continuing the fast of the rats for a further 24 hours. Twenty-four hours after the administration of the carbon tetrachloride, solutions of 300 milligrams of the several sucrose derivatives obtained in the hereinafter-given Examples 1 - 3 in 2 milliliters of isotonic salt solutions were intravenously administered to the rats. This treatment was performed three times at intervals of 8 hours (AS administered groups). On the other hand, the control group was administered in like manner but with 2 milliliters of only isotonic salt solutions. Forty-eight hours after the administration of the carbon tetrachloride, blood was taken from the abdominal aorta of the rats of the several groups, and the GOT and GPT in the blood plasma were measured by the aforementioned methods. Further, a histopathological examination was conducted by fixing the liver with 10% formalin and dyeing with hematoxylin eosin. The results obtained are shown in Tables 3 and 4, below.

Table 3

|  | Administration of Carbon tetrachloride | | Control Group | AS Administered Groups | | |
| --- | --- | --- | --- | --- | --- | --- |
|  | Before Administration | 24 Hours After Administration |  | Example 1 | Example 2 | Example 3 |
| GOT (Karmen U.) | 110±21 | 2015±357 | 2608±385 | 1581±256* | 1628±249* | 1548±234* |
| GPT (Karmen U.) | 34±8 | 930±154 | 967±164 | 554±164* | 476±95* | 310±51* |

Average value ± S.E.
*P < 0.05
AS Administered groups: Sucrose derivatives

Table 4

HISTOPATHOLOGICAL FINDINGS
(number of rats)

|  | Control | AS Administered Groups | | |
| --- | --- | --- | --- | --- |
|  |  | Example 1 | Example 2 | Example 3 |
| Balloon cells |  |  |  |  |
| Intense degree | 6 | 0 | 0 | 0 |
| Medium degree | 3 | 4 | 3 | 2 |
| Light degree | 1 | 5 | 5 | 7 |
| Normal | 0 | 1 | 2 | 1 |
| Zonal necrosis |  |  |  |  |
| Intense degree | 7 | 0 | 0 | 0 |
| Medium degree | 2 | 1 | 2 | 1 |
| Light degree | 1 | 7 | 5 | 6 |
| Normal | 0 | 2 | 3 | 2 |

AS administered groups: Sucrose derivatives.

As shown in Table 3, above, the GOT and GPT of the blood plasma of rats 24 hours after administration of carbon tetrachloride were about thirty times that of the normal values, and it could thus be clearly seen that hepatic disorders had developed as a result of the administration of the carbon tetrachloride. Whereas there was practically no improvement in the GOT and GPT values in the control group which used only an isotonic salt solution for the treatment of the rats suffering from hepatic disorders, there was noted a significant improvement in the case of the groups where the sucrose derivatives were used. Further, when the state of local death of cells was examined, there was noted in the histopathological findings, as shown in Table 4, above, a marked development of balloon cells in the control group. In contrast, there was a marked improvement of this condition in the groups administered the sucrose derivatives. Further, when a comparison is made of the degree of local death of cells, it can be appreciated that there was a conspicuous improvement in the case of the groups where the sucrose derivatives were used.

It can thus be appreciated that the invention disaccharide derivatives possess excellent curative effects.

III. Fatty liver induced by ethionamide.

Groups each of 10 female Wistar rats of body weight 80 – 100 grams were used. The rats were reared for seven days with a feed containing 0.3% of ethionamide.

During the period the rats were being reared with the ethionamide feed, the rats were intravenously administered once daily with solutions of 400 milligrams of the sucrose derivatives obtained in Examples 1 – 3 in 2.0 milliliters of isotonic salt solutions (AS administered groups). The rats of the control group were administered with 2.0 milliliters of only an isotonic salt solution. The rats of the several groups, after having been reared for seven days, were then measured for the neutral fat content of their livers. This measurement was carried out in the following manner. The liver, after being extracted from the rat, was homogenized in acetone and then filtered. The filtrate was evaporated to dryness, after which the resulting residue was dissolved in a 5:5:2 n-hexane-ether-ethanol solvent mixture. After filtering off the insolubles, the filtrate was evaporated to dryness. Next, the resulting residue was dissolved in a small quantity of ether and extracted with a 10-fold amount of acetone for 18 hours at −20° C., after which the extract was evaporated to dryness. The results obtained are shown in Table 5, below.

IV. Radiation damage.

Groups each of 30 8-week old male ddY mice were used. The mice were placed in acrylic resin box of 17 × 17 × 2.5 cm size, and were then exposed to 650 r of 160 kg X-rays (Cu 0.3 mm + Al 0.5 mm filter, dose rats 26.3 r/min), the whole body of the mice being exposed. Sixty minutes before the exposure, one group of mice was abdominally administered a solution of 500 milligrams of the sucrose derivative obtained in Example 2 in 2 milliliters of an isotonic salt solution (AS administered group). On the other hand, the mice of the control group were abdominally administered with 2 milliliters of only the isotonic salt solution. The state of survival of the mice was then examined for a period of 30 days after the exposure to X-rays. The results obtained are shown in the accompanying FIG. 1 and the following Table 6.

Table 6

|  | 14th Day | 16th Day | 18th Day |
|---|---|---|---|
| Control group (Number of survivals/ total number) | 3/30 | 1/30 | 0/30 |
| AS administered group (Number of survivals/ total number) | 12/30 | 9/30 | 8/30 |

It can be seen from the figure and the table that the rate of survival of the group administered the sucrose derivatives of this invention was significantly higher than that of the control group.

The following experiment illustrates that greater phrmacological effects are had by using the invention disaccharide derivatives in conjunction with other medicines, especially the glutathiones instead of using either of these medicines alone.

V. The conjoint use of glutathione in the case of experimental hepatitis induced by D-galactosamin.

The effects obtained by using injection mixtures of either a reduced type glutathione or an oxidized type Table 5

|  | Normal value | Control Group | Example 1 | Example 2 | Example 3 |
|---|---|---|---|---|---|
| Hepatic neutral fat (mg/g wet liver) | 10.0±0.5 | 32.3±2.0 | 18.1±2.6* | 16.3±2.5* | 20.4±3.4* |

Average value ± S.E.
*P < 0.01
AS: Sucrose derivative

As shown in Table 5, above, in the case of the control group, a marked increase in hepatic neutral fat as a result of the development of fatty liver was noted. In contrast, it can be appreciated that the tendency to an increase in hepatic neutral fat has been checked to a marked degree in the case of the groups administered the sucrose derivatives of this invention.

Next, a description will be made of an experiment that was conducted for judging the effects that the invention disaccharide derivatives have in affording protection against radiation damage.

glutathione and a sucrose derivative obtained by the method of preparing a pharmaceutical composition of the hereinafter-given Example 11 in treating animals suffering from hepatitis induced by D-galactosamin were tested by operating as in I., above. As can be seen from the results of the following Table 7, the effects obtained in treating hepatitis were far greater in the case where an injection mixture of the sucrose derivative and the glutathione were used at the rate of 2 ml/rat than in the case where these substances were used independently at a rate of 75 mg/rat of the sucrose derivative and 5 mg/rat of the glutathione.

Table 7

|  | Control Group | GSH Administered Group (5 mg/rat) | GSSH Administered Group (5 mg/rat) | AS Administered Group (75 mg/rat) | GSH Mixture Administered Group (GSH 5 mg/rat) (AS 75 mg/rat) | GSSH Mixture Administered Group (GSSH 5 mg/rat) (AS 75 mg/rat) |
|---|---|---|---|---|---|---|
| GOT (Karmen U.) | 2748±490 | 2510±510 | 2650±550 | 1720±340 | 745±76 | 666±80 |

Table 7-continued

|  | Control Group | GSH Administered Group (5 mg/rat) | GSSH Administered Group (5 mg/rat) | AS Administered Group (75 mg/rat) | GSH Mixture Administered Group (GSH 5 mg/rat) (AS 75 mg/rat) | GSSH Mixture Administered Group (GSSH 5 mg/rat) (AS 75 mg/rat) |
|---|---|---|---|---|---|---|
| GPT (Karman U.) | 1830±432 | 1660±472 | 1720±427 | 738±242 | 176±35 | 154±42 |

Average value ± S.E.
GSH: Reduced type glutathione
GSSH: Oxidized type glutathione
AS: Sucrose derivatives (Example 2)

The results of few experiments that were carried out on man for judging the pharmacological effects obtained by the use of the disaccharide derivatives of this invention in treating the hepatic and allergic diseases will be given.

VI. Clinical tests with respect to the various hepatic diseases.

The therapy was carried out by the intravenous injection of 10 – 20 milliliters (500 – 1000 milligrams) of a 20% glucose solution containing 5 w/v% of a sucrose derivative obtained by the method of preparing pharmaceutical compositions of Example 11. The judgment of the effects was based on subjective and objective observations as well as the various functional tests of the liver and measurements of the blood plasma GOT and GPT.

(1) Effects on the subjective and objective symptoms.

As can be seen in Table 8, the complaints such as lack of appetite and feeling of fatigue as seen in the case of liver troubles improved relatively promptly with the start of the AS therapy. Especially, in the case of the appetite, in most cases there was clearly an improvement in two or three days after commencing the treatment. On the other hand, as regards the objective symptoms, there were many cases where the swelling of the liver was reduced.

(2) Effects on liver function.

As shown in Table 9, below, as regards the T.T.T. reaction, a tendency to a decrease and normalization was noted in the several disorders. As regards the A/G ratio, a tendency to an increase and normalization was also noted in all cases. Further, the icteric index exhibited a decrease and normalization in all cases. Again, there was noted a marked decrease and normalization of the GOT and GPT values.

Table 9

| Disorder | Sex | Age | Dose and number of days mg/days | T.T.T. Before | T.T.T. After | Unit Icteric index Before | Icteric index After | A/G ratio Before | A/G ratio After | GOT Karmen U Before | GOT Karmen U After | GPT Karmen U Before | GPT Karmen U After |
|---|---|---|---|---|---|---|---|---|---|---|---|---|---|
| Acute hepatitis | ♂ | 34 | 1000/14 | 2.2 | 1.7 | 40 | 8 | 1.07 | 1.18 | 624 | 220 | 760 | 120 |
|  | ♀ | 24 | 1000/14 | 2.5 | 20 | 50 | 15 | 1.05 | 1.04 | 160 | 72 | 336 | 61 |
| Chronic hepatitis | ♂ | 27 | 500/21 | 1.2 | 0.5 | 6 | 5 | 1.11 | 1.20 | 158 | 87 | 122 | 57 |
|  | ♂ | 45 | 500/21 | 11.0 | 10.1 | 8 | 4 | 1.03 | 1.15 | 167 | 62 | 148 | 48 |
| Hepato-cirrhosis | ♂ | 42 | 500/21 | 9.5 | 5.2 | 4 | 4 | 0.52 | 0.66 | 141 | 130 | 122 | 118 |
|  | ♂ | 57 | 500/21 | 9.1 | 7.7 | 6 | 5 | 0.70 | 0.89 | 120 | 96 | 113 | 108 |

VII. Clinical tests with respect to the various allergic diseases.

The therapeutic treatments were carried out by the method of intravenously injecting 10 – 20 milliliters (500 – 1000 milligrams) of a 20% glucose solution containing 5 w/v% of the sucrose derivative obtained by the method of preparing pharmaceutical compositions of the hereinafter-given Example 11. The results were judged by the subjective and objective observations before and after the treatment, i.e., the effect of stopping itchiness and the decrease and disappearance of rash and eczema.

As is apparent from the results given in Table 10, below, when the sucrose derivative of this invention was administered to patients suffering from such inflammatory skin diseases as toxic eruptions, acute urticaria and chronic eczema, marked effects or at least appreciable effects were exhibited in all cases.

Table 8

| Disorder | Sex | Age | Dose and number of days mg/days | Appetite Before | Appetite After | Fatigue feeling Before | Fatigue feeling After | Swelling of liver Before | Finger breadth) After |
|---|---|---|---|---|---|---|---|---|---|
| Acute hepatitis | ♂ | 34 | 1000/14 | poor | good | ± | − | 1 | 0 |
|  | ♀ | 24 | 1000/14 | poor | good | + + | − | 1 | 0 |
| Chronic hepatitis | ♂ | 27 | 500/21 | poor | good | + | − | 2 | 2 |
|  | ♂ | 45 | 500/21 | poor | poor | + | − | 2 | 0 |
| Hepato-cirrhosis | ♂ | 42 | 500/21 | poor | poor | + + | + | 0 | 0 |
|  | ♀ | 57 | 500/21 | poor | good | + | ± | 0 | 0 |

+ + Intense degree
+ Medium
± Light degree
− Normal

Table 10

| Disease | Number of Cases | Dose and Number of Days mg/days | Itch Stopping Effect Marked | Itch Stopping Effect Appreciable | Curative Effect Marked | Curative Effect Appreciable |
|---|---|---|---|---|---|---|
| Toxic eruption | 5 | 1000/7 | 1 | 4 | 3 | 2 |
| Acute urticaria | 2 | 500/3 | 1 | 1 | 2 | 0 |
| Chronic eczema | 4 | 1000/10 | 0 | 4 | 3 | 1 |

As is apparent from the foregoing animal experiments and clinical tests, the disaccharide derivatives of this invention can be effectively used for the therapy and treatment of the hepatic and allergic diseases and radiation damage.

The $LD_{50}$ values of the invention disaccharide derivatives obtained in the hereinafter-given Examples 1 - 3, and which were those used in the foregoing experiments, were as shown in Table 11, below.

Table 11

|  | Example 1 | Example 2 | Example 3 |
|---|---|---|---|
| $LD_{50}$ | 20.5 g/kg | 22.7 g/kg | 24.3 g/kg |

Figure 12:
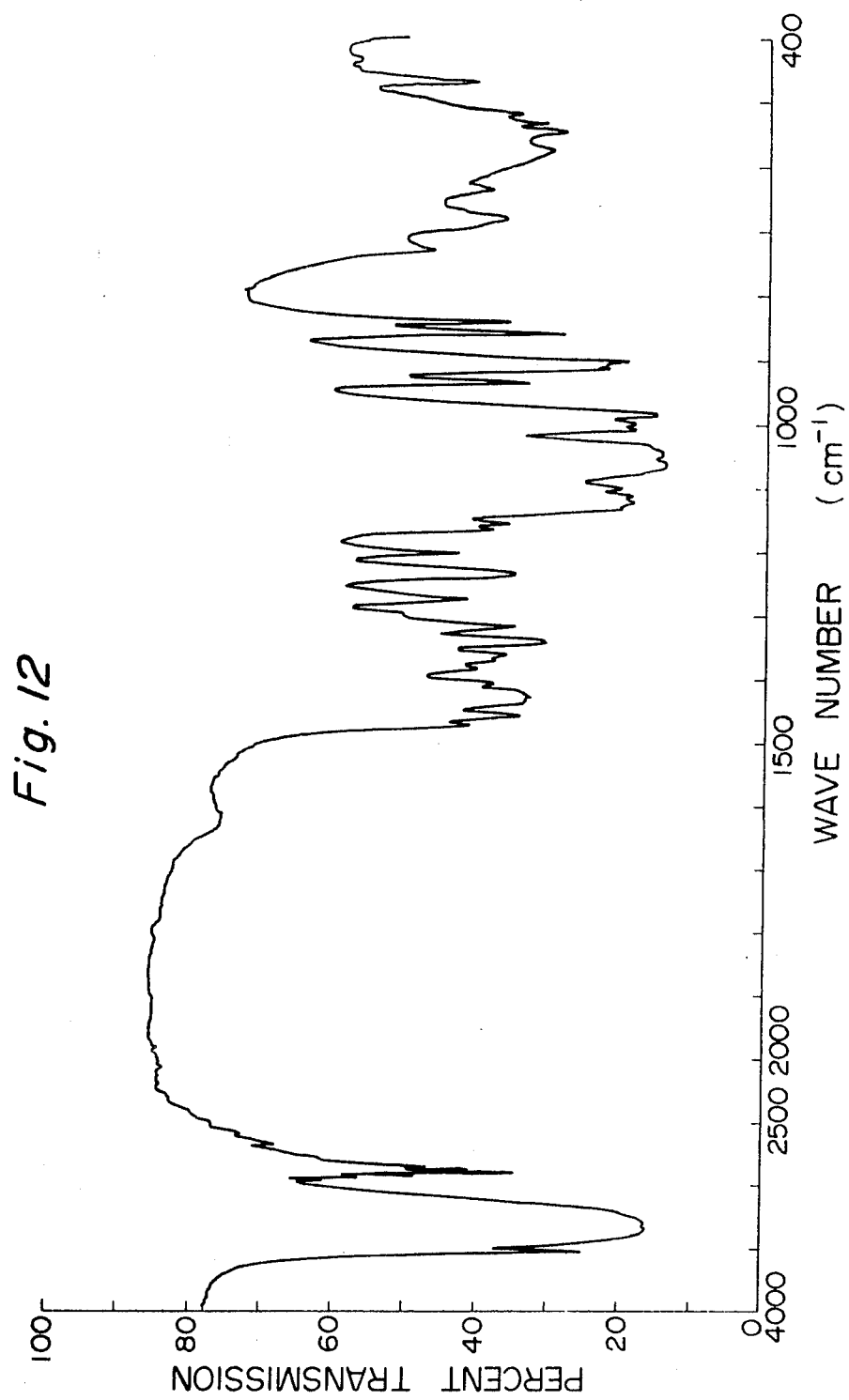
Figure 13:
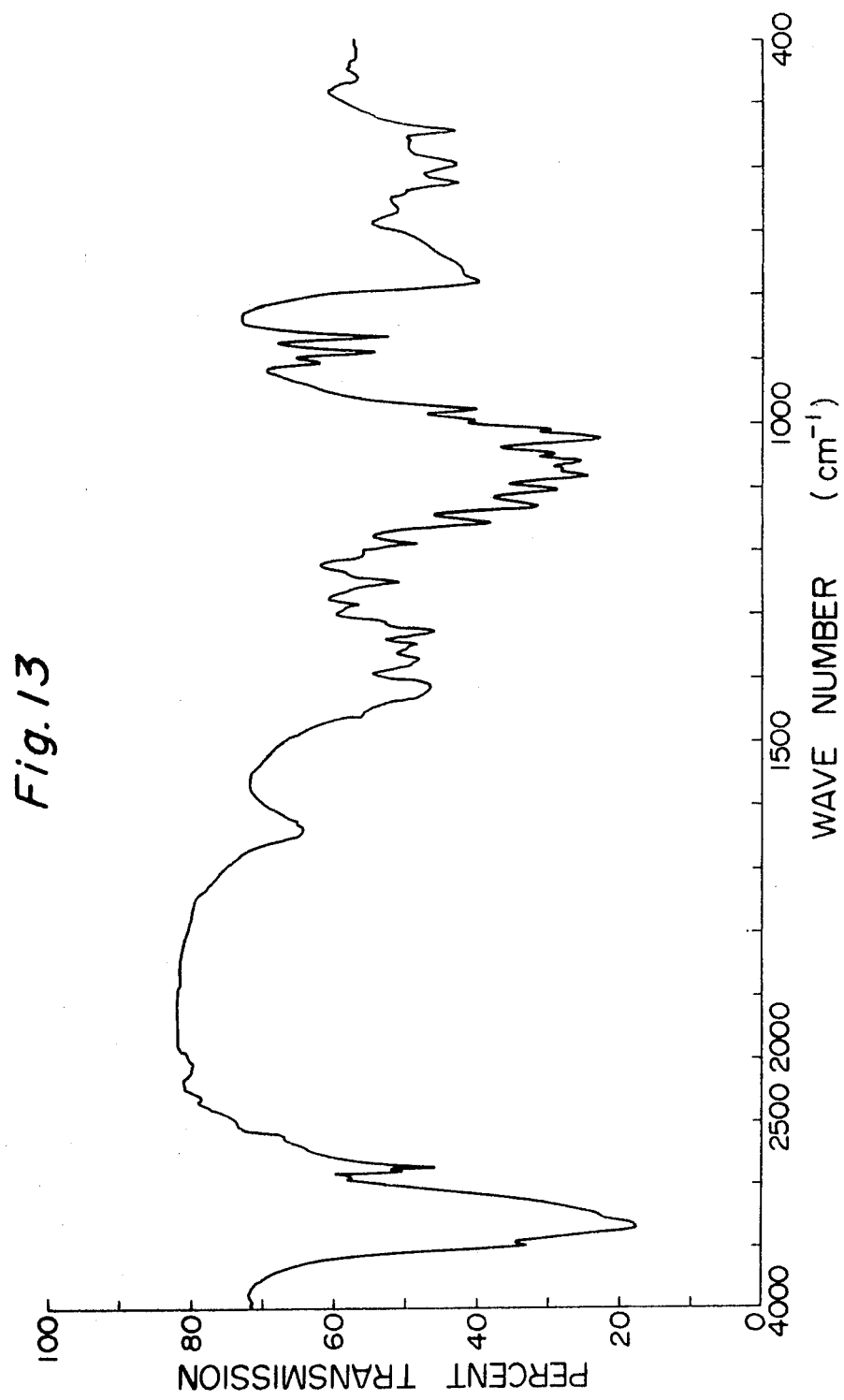
Figure 14:
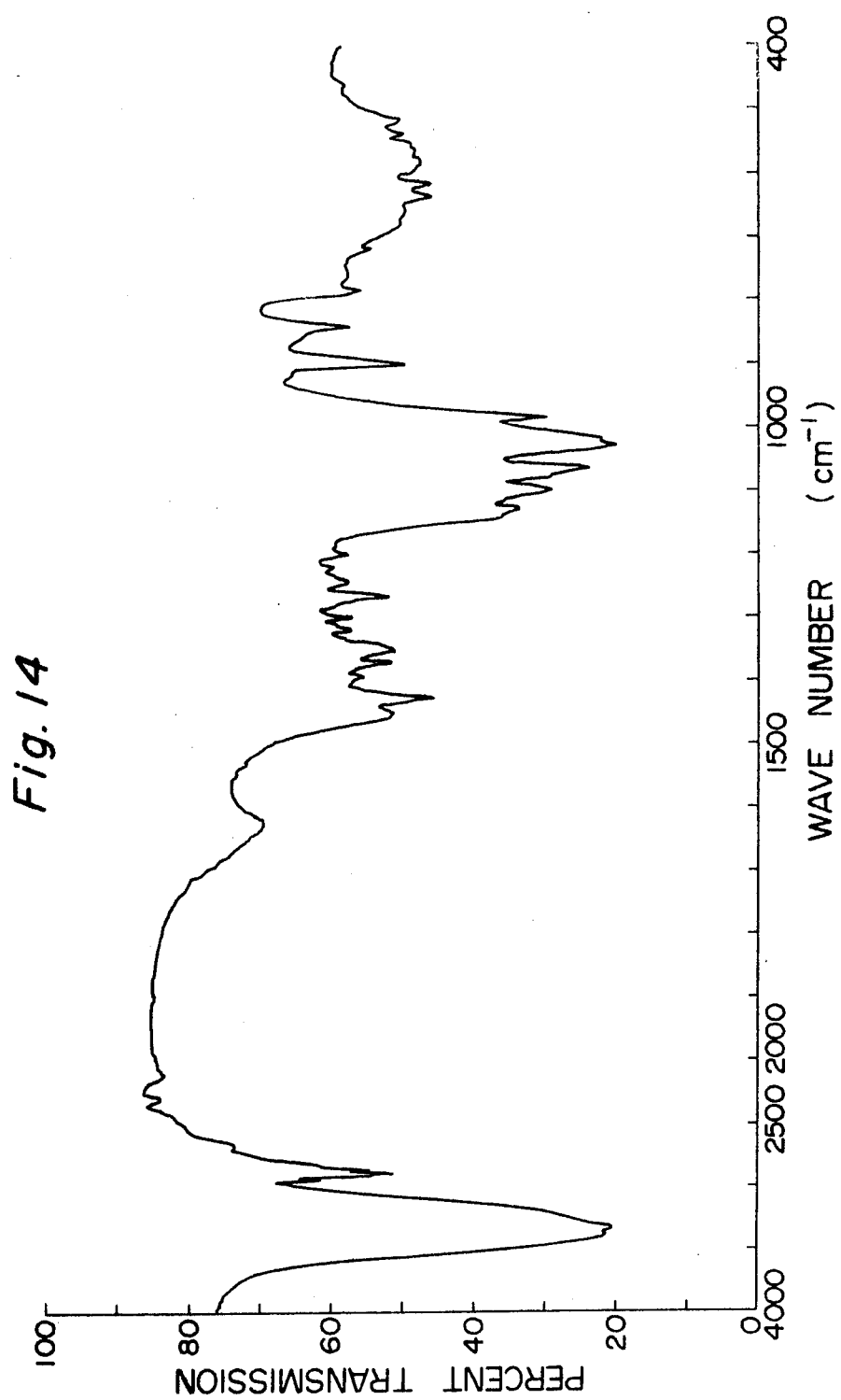

As previously stated, the disaccharide derivatives of this invention are usually white or light yellowish powders characterized by an infrared absorption spectrum with bands in at least one of the neighborhoods of 1680 cm$^{-1}$, 1715 cm$^{-1}$ and 1750 cm$^{-1}$. This is shown in the accompanying drawings; wherein FIGS. 2 - 11 are infrared absorption spectrograms of the disaccharide derivatives obtained in Examples 1 - 10. On the other hand, FIGS. 12 - 14 are infrared absorption spectrograms of sucrose, lactose and maltose that have been used as the starting material.

As is apparent from these figures, characteristic absorptions are exhibited in the neighborhood of 1680 cm$^{-1}$ in the case of the sucrose derivative of Example 1, in the neighborhood of 1750 cm$^{-1}$ in the case of the sucrose derivative of Example 2, in the neighborhood of 1715 cm$^{-1}$ in the case of the sucrose derivative of Example 3, in the neighborhood of 1680 cm$^{-1}$ and 1715 cm$^{-1}$ in the case of the sucrose derivative of Example 4, in the neighborhood of 1715 cm$^{-1}$ in the case of the sucrose derivative of Example 5, in the neighborhood of 1715 cm$^{-1}$ in the case of the maltose derivative of Example 6, in the neighborhood of 1715 cm$^{-1}$ in the case of the sucrose derivative of Example 7, in the neighborhood of 1715 cm$^{-1}$ in the case of the lactose derivative of Example 8, in the neighborhood of 1750 cm$^{-1}$ and 1680 cm$^{-1}$ in the case of the sucrose derivative of Example 9, and in the neighborhood of 1715 cm$^{-1}$ in the case of the sucrose derivative of Example 10. These absorptions are also seen in the respective infrared absorption spectra of sucrose, lactose and maltose.

The following examples will serve to more fully illustrate the process of preparing the invention compound and pharmaceutical composition of the present invention.

EXAMPLE 1

Fifty grams of sucrose is dissolved in 325 milliliters of a 0.045 M sodium bicarbonate solution. After cooling the solution to 0° C., 25 grams of cyanogen bromide is added, following which the pH of the solution is promptly adjusted to 11.0 by adding a 4 N sodium hydroxide solution. The solution is then stirred for 80 minutes at below 10° C. while holding the pH at 10.9 - 11.1 by the addition dropwise of a 4 N sodium hydroxide solution.

The solution is then poured into 2 liters of cold acetone to obtain a white precipitate, which is washed in 500 milliliters each of acetone and methanol in the order given and thereafter vacuum dried to obtain 35 grams of a white powdery product. The N content of this product is 5.5%, and its inherent viscosity is 0.045 dl/g.

EXAMPLE 2

Fifty grams of sucrose is dissolved in 325 milliliters of a 0.045 M sodium bicarbonate solution. After cooling the solution to 0° C., 25 grams of cyanogen bromide is added, following which the pH of the solution is promptly adjusted to 11.0 by adding a 4 N sodium hydroxide solution. The solution is then stirred for 20 minutes at below 10° C. while holding the pH at 10.9 - 11.1 by the addition dropwise of a 4 N sodium hydroxide solution.

Next, the solution is introduced into 2 liters of acetone to obtain a precipitate, which is dissolved with stirring in 500 milliliters of an aqueous medium of pH 5.0 containing 30 milliliters of glacial acetic acid and 14 grams of sodium hydroxide, after which the resulting solution is held for 18 hours at 25° C.

1.5 Liters of acetone is then added to the solution to obtain a white precipitated, which is purified by reprecipitation by dissolving the precipitate in 400 milliliters of water and adding of 1.5 liters of acetone. The product is then powderized with methanol and thereafter vacuum dried to obtain 33 grams of a white powdery product whose N content is 3.8% and inherent viscosity is 0.047 dl/g.

EXAMPLE 3

Fifty grams of sucrose is dissolved in 325 milliliters of a 0.045 M sodium bicarbonate solution. After cooling the solution to 0° C., 25 grams of cyanogen bromide is added, following which the pH of the solution is promptly adjusted to 11.0 by the addition of a 4 N sodium hydroxide solution. The solution is then stirred for 20 minutes at below 10° C. while holding the pH of the solution at 10.9 - 11.1 by the addition dropwise of a 4 N sodium hydroxide solution.

This is followed by introducing the solution into 2 liters of acetone to obtain a precipitate, which is dissolved with stirring in 250 milliliters of an aqueous medium of pH 8.5 containing 4.2 grams of sodium bicarbonate followed by holding the solution for 10 hours at 25° C. One liter of acetone is then added to the solution to obtain a white precipitate, which is purified by reprecipitation by dissolving the precipitate in 200 milliliters of water and adding 1.0 liter of acetone. The product is then powderized with a 1:2 methanol-acetone mixture and thereafter vacuum dried to obtain 13 grams of a white powdery product. The N content of this product is 7.2%, and its inherent viscosity is 0.033 dl/g.

EXAMPLE 4

Fifty grams of sucrose is dissolved in 500 milliliters of a 0.1 M sodium bicarbonate solution, to which is then added 500 milliliters of a cold water solution containing 50 grams of cyanogen bromide, after which the pH of the solution is promptly adjusted to 11.0 by the addition of a 4 N sodium hydroxide solution. This is followed by stirring the solution for 15 minutes at below 7° C, while holding the pH at 10.9 – 11.1 by the addition of a 4 N sodium hydroxide solution. The precipitate separating out is then filtered off, washed with 500 milliliters each of water, methanol and acetone in the order given and thereafter vacuum dried to obtain 41 grams of a white powdery product whose N content is 4.5% and inherent viscosity if 0.020 dl/g.

EXAMPLE 5

Fifty grams of sucrose is dissolved in 250 milliliters of a 0.1 M sodium bicarbonate solution, after which 500 milliliters of an aqueous solution containing 30 grams of cyanogen chloride is added thereto. Next, the solution is stirred for 30 minutes at below 10° C. while maintaining the pH at 10.9 – 11.1 by adding dropwise a 4 N sodium hydroxide solution, after which the solution is allowed to stand for 24 hours at room temperature. This is followed by introducing the solution into 2.5 liters of acetone to form a precipitate, purifying the resulting precipitate by dissolving it in 300 milliliters of water and adding 1.5 liters of acetone to again form a precipitate, followed by powderizing the precipitate with methanol and thereafter vacuum drying the powder to obtain 15 grams of a white powdery product whose N content is 6.9% and inherent viscosity if 0.027 dl/g.

EXAMPLE 6

Fifty grams of maltose is dissolved in 350 milliliters of a 0.05 M sodium bicarbonate solution and, after cooling the solution to 0° C., 30 grams of cyanogen bromide is added thereto. The pH of the solution is then promptly adjusted to 11.0 by the addition of a 4 N sodium hydroxide solution. Next, the solution is stirred for 20 minutes at below 10° C. while holding the pH at 10.9 – 11.1 by the dropwise addition of a 4 N sodium hydroxide solution, after which the solution is introduced into 2 liters of acetone to obtain a precipitate.

This is followed by dissolving the resulting precipitate with stirring in 330 milliliters of an aqueous medium containing 14 grams of sodium bicarbonate, following which 1.5 liters of acetone is added to the resulting solution to form a light yellow precipitate, which is then dissolved in 30 milliliters of water. Next, gel filtration of this solution is carried out with a Sephadex G-25 column using water as solvent to collect an eluate portion having an ultraviolet absorption of 215 mµ, which is freeze-dried to obtain 20 grams of a light yellow powdery product. This product has an N content of 5.8% and an inherent viscosity of 0.039 dl/g.

EXAMPLE 7

Fifty grams of sucrose is dissolved in 350 milliliters of a 0.05 M sodium bicarbonate solution, after which the solution is cooled to 0° C., and 43 grams of phenyl cyanate is added thereto. Next, the experiment is operated as in Example 3 to obtain 15 grams of a white powdery product having an N content of 6.4% and an inherent viscosity of 0.039 dl/g.

EXAMPLE 8

Fifty grams of lactose is dissolved in 350 milliliters of a 0.05 M sodium bicarbonate solution, after which the solution is cooled to 0° C., and 40 grams of cyanogen bromide is added thereto. This is followed by operating the experiment as in Example 3 to obtain 12 grams of a light yellow powdery product whose N content is 6.0% and inherent viscosity is 0.033 dl/g.

EXAMPLE 9

Fifty grams of sucrose is dissolved in 325 milliliters of a 0.045 M sodium bicarbonate solution and, after cooling the resulting solution to 0° C., 25 grams of cyanogen bromide is added thereto. Next, the pH of the solution is promptly adjusted to 11.0 by the addition of a 4 N sodium hydroxide solution, following which the solution is stirred for 20 minutes at below 10° C. while holding the pH at 10.9 – 11.1 by the addition dropwise of a 4 N sodium hydroxide solution.

Next, the solution is introduced into 2 liters of acetone to form a precipitate, which is dissolved in 500 milliliters of a dilute hydrochloric acid solution with stirring and held for 18 hours at 25° C. and a pH of 4.5.

Thereafter, by operating as in Example 2 30 grams of a white powdery product is obtained. This product has an N content of 3.9% and an inherent viscosity of 0.046 dl/g.

EXAMPLE 10

Fifty grams of sucrose is dissolved in 400 milliliters of dimethyl sulfoxide, after which 250 milliliters of triethylamine and 150 milliliter of dioxane are added thereto, and the solution is cooled to −2° C. Next, while maintaining the reaction temperature at below 5° C. 90 milliliters of ethyl chlorocarbonate is added dropwise over a 15-minute period. Ten minutes after completion of the dropping, the reaction solution is introduced into 1.5 liters of ethyl ether. After washing the resulting precipitate twice in 500 milliliters of ethyl ether, 75 milliliters of 95% ethanol is added thereto, after which the insolubles separating out are filtered off. Four hundred milliliters of ether is then added to the filtrate, and a precipitate is obtained. After adding 50 milliliters of concentrated ammonia water to the so obtained precipitate, followed by stirring the mixture to effect the dissolution of the precipitate in the ammonia water, 500 milliliters of acetone is added to the solution to form a precipitate, which is purified by reprecipitation by dissolving the precipitate in 100 milliliters of water and adding 500 milliliters of acetone to the resulting solution. After powderizing the resulting precipitate with ethanol, the resulting powder is vacuum dried to obtain 25 grams of a white powdery product having an N content of 4.6% and an inherent viscosity of 0.026 dl/g.

EXAMPLE 11

Preparation of pharmaceutical composition.

| Tablets | Weight (grams) |
|---|---|
| Sucrose derivative (Example 4) | 250 |
| Lactose | 140 |
| Polyvinyl pyrrolidone | 40 |
| Talc | 50 |
| Starch | 20 |

The sucrose derivative and lactose are blended and then passed through a 60-mesh sieve (U.S. Standard).

Next, the mixture is wetted with alcoholic polyvinyl pyrrolidone and passed through a 12-mesh sieve to form the granules, which are then dried. After grading the dried granules by passing them through a 16-mesh sieve, talc and starch are added, after which the mixture is made into a single tablet of 500-milligram weight.

| Granular preparation | Weight (grams) |
|---|---|
| Sucrose derivative (Example 3) | 250 |
| Methyl cellulose | 150 |
| Corn starch | 80 |
| Polyvinyl pyrrolidone | 20 |
| Flavor | small amount |

The sucrose derivative, methyl cellulose, flavor and corn starch are commingled and then passed through a 60-mesh sieve. After wetting the mixture with alcoholic polyvinyl pyrrolidone, it is formed into granules with a stainless steel sieve having holes 0.7 millimeters in diameter.

| Injection (1) | |
|---|---|
| Sucrose derivative (Example 2) | 3.75 grams |
| Reduced type glutathione (or oxidized type glutathione) | 0.25 grams |
| Glucose | 20 grams |
| Distilled water for injection use | suitable amount |
| | 100 milliliters |

The sucrose derivative, glutathione and glucose are dissolved in the distilled water for injection use, after which the latter is further added to make up 100 milliliters of the solution followed by making the solution into an injection in customary manner.

| Injection (2) | |
|---|---|
| Sucrose derivative (Example 2) | 5 grams |
| Glucose | 20 grams |
| Distilled water for injection use | suitable amount |
| | 100 milliliters |

The sucrose derivative and glucose are dissolved in the distilled water for injection use, after which the latter is furthered added to make up 100 milliliters of the solution followed by making the solution into an injection in customary manner.

We claim:

1. A composition which is a mixture of the reaction products of a disaccharide selected from the group consisting of sucrose, maltose, lactose and isomaltose with an activating agent selected from the group consisting of cyanogen bromide, cyanogen iodide, cyanogen chloride, phenyl cyanate, 2,2,2-trichloroethyl cyanate, chlorocarbonic acid lower alkyl ester and bromocarbonic acid lower alkyl ester.

2. The composition of claim 1 which is a mixture of the reaction products of the disaccharide and the activating agent at a weight ratio of disaccharide to activating agent of from about 1:0.1 to about 1:3.5.

3. The composition of claim 1 which is a mixture of the reaction products of the disaccharide and activating agent in an aqueous or organic solvent selected from the group consisting of methanol, ethanol, dimethyl sulfoxide, tetrahydrofuran, dioxane, toluene, chloroform and ethyl acetate or mixtures thereof at a concentration of disaccharide of from about 10% to about 20% weight/solvent volume, and at a concentration of activating agent of from about 5% to about 15% weight/solvent volume.

4. The composition of claim 3 which is a mixture of the reaction products of the disaccharide and an activating agent selected from the group consisting of cyanogen bromide, cyanogen iodide, cyanogen chloride, phenyl cyanate and 2,2,2-trichloroethyl cyanate in a solvent selected from the group consisting of water, methanol and ethanol or a mixture of water and methanol or ethanol at a pH of about 9 to about 12 at a reaction temperature up to about 40° C.

5. The composition of claim 4 wherein the mixture of the reaction products has an inherent viscosity of from about 0.018 to about 0.080 dl/g and an infrared spectrum which exhibits an absorption band at at least one wavelength in the neighborhoods of 1680 $cm^{-1}$, 1715 $cm^{-1}$ and 1750 $cm^{-1}$.

6. The composition of claim 5 in which the activating agent is cyanogen bromide, cyanogen iodide or cyanogen chloride.

7. The composition of claim 5 in which the activating agent is phenyl cyanate or 2,2,2-trichloroethyl cyanate.

8. The composition of claim 3 which is a mixture of the reaction product of the disaccharide and, as activating agent, chlorocarbonic acid lower alkyl ester or bromocarbonic acid lower alkyl ester in an organic solvent selected from the group consisting of dimethyl sulfoxide, tetrahydrofuran, dioxane, toluene, chloroform and ethyl acetate or mixtures thereof at a reaction temperature of about $-15°$ C to about 30° C in the presence of $C_1$-$C_4$ trialkylamine.

9. The composition of claim 8 wherein the mixture of the reaction products has an inherent viscosity of from about 0.018 to about 0.080 dl/g and an infrared spectrum which exhibits an absorption band at at least one wavelength in the neighborhoods of 1680 $cm^1$, 1715 $cm^{-1}$ and 1750 $cm^1$.

10. A pharmaceutical composition containing, as the active ingredient, the composition of claim 1 and a pharmaceutically acceptable diluent, the active ingredient comprising from about 1 to about 90% by weight of the composition.

11. A pharmaceutical composition containing, as the active ingredient, the composition of claim 6 and a pharmaceutically acceptable diluent, the active ingredient comprising from about 1 to about 90% by weight of the composition.

12. The pharmaceutical composition of claim 11 in which the disaccharide is sucrose.

13. A pharmaceutical composition containing, as the active ingredient, the composition of claim 7 and a pharmaceutically acceptable diluent, the active ingredient comprising from about 1 to about 90% by weight of the composition.

14. The composition of claim 8 in which the activating agent is methyl chlorocarbonate, ethyl chlorocarbonate or ethyl bromocarbonate.

15. A pharmaceutical composition containing as the active ingredient, the composition of claim 9 and a pharmaceutically acceptable diluent, the active ingredient comprising from about 1 to about 90% by weight of the composition.

16. The pharmaceutical composition of claim 15 in which the disaccharide is sucrose.

17. A method of treating hepatic diseases including acute hepatitis, cholangiolitic hepatitis, fatty liver, drug-induced hepatic injury and hepato-cirrhoses or intoxication which comprises administering to animals suffering from hepatic disease from about 5 milligrams to about 250 milligrams per kilogram body weight per day of the pharmaceutical composition of claim 10.

18. A method of treating hepatic diseases including acute hepatitis, cholangiolitic hepatitis, fatty liver, drug-induced hepatic injury and hepato-cirrhoses or intoxication which comprises administering to animals suffering from hepatic disease from about 5 milligrams to about 250 milligrams per kilogram body weight per day of the pharmaceutical composition of claim 11.

19. A method of treating hepatic diseases including acute hepatitis, cholangiolitic hepatitis, fatty liver, drug-induced hepatic injury and hepato-cirrhoses or intoxication which comprises administering to animals suffering from hepatic disease from about 5 milligrams to about 250 milligrams per kilogram body weight per day of the pharmaceutical composition of claim 12.

20. A method of treating hepatic diseases including acute hepatitis, cholangiolitic hepatitis, fatty liver, drug-induced hepatic injury and hepato-cirrhoses or intoxication which comprises administering to animals suffering from hepatic disease from about 5 milligrams to about 250 milligrams per kilogram body weight per day of the pharmaceutical composition of claim 13.

21. A method of treating hepatic diseases including acute hepatitis, cholangiolitic hepatitis, fatty liver, drug-induced hepatic injury and hepato-cirrhosis or intoxication which comprises administering to animals suffering from hepatic disease from about 5 milligrams to about 250 milligrams per kilogram body weight per day of the pharmaceutical composition of claim 15.

* * * * *